United States Patent
Cech et al.

(10) Patent No.: US 9,636,012 B2
(45) Date of Patent: May 2, 2017

(54) OPHTHALMIC LENS ASSEMBLIES AND METHODS OF ASSEMBLY AND USE

(71) Applicant: Volk Optical Inc., Mentor, OH (US)

(72) Inventors: Steven D. Cech, Aurora, OH (US); John Pysarchuk, Cleveland Heights, OH (US)

(73) Assignee: Volk Optical Inc., Mentor, OH (US)

( * ) Notice: Subject to any disclaimer, the term of this patent is extended or adjusted under 35 U.S.C. 154(b) by 0 days.

(21) Appl. No.: 14/865,090

(22) Filed: Sep. 25, 2015

(65) Prior Publication Data
US 2016/0089022 A1   Mar. 31, 2016

Related U.S. Application Data

(60) Provisional application No. 62/056,083, filed on Sep. 26, 2014.

(51) Int. Cl.
| | |
|---|---|
| *A61B 3/10* | (2006.01) |
| *A61B 3/117* | (2006.01) |
| *A61B 3/125* | (2006.01) |
| *G02B 5/09* | (2006.01) |
| *A61B 19/02* | (2006.01) |

(52) U.S. Cl.
CPC .............. *A61B 3/117* (2013.01); *A61B 3/125* (2013.01); *G02B 5/09* (2013.01); *A61B 2019/022* (2013.01); *A61B 2019/0242* (2013.01); *A61B 2562/12* (2013.01)

(58) Field of Classification Search
CPC .............. A61B 3/102; A61B 3/13; A61B 3/00
USPC ........ 351/219, 220, 221, 246, 205, 200, 216
See application file for complete search history.

(56) References Cited

U.S. PATENT DOCUMENTS

| | | | |
|---|---|---|---|
| 3,944,341 | A | 3/1976 | Pomerantzeff |
| 4,033,679 | A | 7/1977 | Sussman |
| 4,134,647 | A | 1/1979 | Ramos-Caldera |
| 4,269,307 | A | 5/1981 | LaHaye |
| 5,252,998 | A | 10/1993 | Reis et al. |
| 5,501,217 | A | 3/1996 | Ishiguro et al. |
| 5,548,352 | A | 8/1996 | Dewey |
| 5,784,147 | A | 7/1998 | Volk |
| 5,822,036 | A | 10/1998 | Massie et al. |

(Continued)

OTHER PUBLICATIONS

Search Report pertaining to Application No. PCT/US2015/052192 dated Jan. 12, 2016.

*Primary Examiner* — Hung Dang
(74) *Attorney, Agent, or Firm* — Dinsmore & Shohl LLP

(57) ABSTRACT

Ophthalmic lens assemblies and methods of assembly and use may include a lens assembly including a lens element and a protective cover. The lens element includes a contact lens surface and a faceted optical body including a distal portion and a faceted portion including one or more mirror facets to form a TIR activity pathway. The protective cover includes a contact aperture shaped to receive the contact lens surface, a grip portion, and a facet housing portion including an interior surface. The contact aperture of the protective cover is stretch-fit about a periphery of the contact lens surface to maintain a proximal-side fluid seal. The grip portion of the protective cover is stretch-fit about the distal portion of the lens element to maintain a distal-side fluid seal. One or more TIR-inducing air gaps are defined by the facet housing portion between the interior surface and the mirror facets.

24 Claims, 4 Drawing Sheets

(56) References Cited

U.S. PATENT DOCUMENTS

| | | |
|---|---|---|
| 6,767,098 B2 | 7/2004 | Erickson et al. |
| 6,942,343 B2 * | 9/2005 | Farberov ................ A61B 3/117 |
| | | 351/205 |
| 7,766,480 B1 | 8/2010 | Graham et al. |
| 8,011,504 B1 | 9/2011 | Farberov |
| 8,303,116 B2 | 11/2012 | Heacock |
| 8,596,788 B2 | 12/2013 | Ranchod |
| 8,678,593 B2 | 3/2014 | Abt |
| 2002/0167644 A1 | 11/2002 | Pollack et al. |
| 2010/0118270 A1 | 5/2010 | Shea et al. |
| 2012/0050683 A1 | 3/2012 | Yates |

* cited by examiner

OPHTHALMIC LENS ASSEMBLIES AND METHODS OF ASSEMBLY AND USE

CROSS-REFERENCE TO RELATED APPLICATIONS

This application claims the benefit of U.S. Provisional Application Ser. No. 62/056,083 (VOL 0096 MA), filed Sep. 26, 2014.

BACKGROUND

Field

The present disclosure relates to ophthalmic lens assemblies used to diagnose and treat conditions of eyes, and in particular ophthalmic lens assemblies including a protective cover and a mirrored ophthalmic lens element.

BRIEF SUMMARY

According to the subject matter of the present disclosure, a lens assembly may include a lens element and a protective cover. The lens element may include a contact lens surface and a faceted optical body including a faceted portion and a distal portion. The faceted portion is disposed between the contact lens surface and the distal portion. The faceted portion may include one or more mirror facets including respective one or more internal, optically reflective facets and one or more external facets disposed opposite respective internal, optically reflective facets. The one or more internal, optically reflective facets may include respective one or more total-internal-reflective (TIR) surfaces. The one or more internal, optically reflective facets and the contact lens surface form a pathway for TIR activity. The protective cover may include a contact aperture shaped to receive the contact lens surface, a grip portion, and a facet housing portion including an interior surface and disposed between the contact aperture and the grip portion. The contact aperture of the protective cover may be stretch-fit about a periphery of the contact lens surface to maintain a proximal-side fluid seal. The grip portion of the protective cover may be stretch-fit about the distal portion of the lens element to maintain a distal-side fluid seal. One or more TIR-inducing air gaps may be defined by the facet housing portion of the protective cover between the interior surface of the facet housing portion of the protective cover and the one or more external facets of the faceted portion of the faceted optical body.

In accordance with one embodiment of the present disclosure, a method of assembling and using an ophthalmic lens assembly may include disposing a protective cover about a lens element including one or more mirror facets that include respective TIR surfaces. A contact lens surface of the lens element may be received through a contact aperture of the protective cover. The protective cover may be stretch-fit about a periphery of the contact lens surface to maintain a proximal-side fluid seal. The protective cover may be stretch-fit about a distal portion of the lens element to maintain a distal-side fluid seal. A faceted portion of the lens element including the one or more mirror facets may be disposed between the contact lens surface and the distal portion of the lens element. One or more TIR-inducing air gaps may be defined by the protective cover between an interior surface of the protective cover and the one or more mirror facets of the lens element. The method may further include placing the contact lens surface of the lens element in contact with a portion of a curvature surface of a cornea of an eye, and reflecting illumination into the eye via the TIR surfaces and redirecting light reflected by the eye via the TIR surfaces into a direction for external viewing.

In accordance with another embodiment of the present disclosure, a method of assembling an ophthalmic lens assembly by disposing a protective cover about a lens element including one or more mirror facets that include respective TIR surfaces, wherein a contact lens surface of the lens element may be received through a contact aperture of the protective cover. The protective cover may be stretch-fit about a periphery of the contact lens surface to maintain a proximal-side fluid seal. The protective cover may be stretch-fit about a distal portion of the lens element to maintain a distal-side fluid seal. A faceted portion of the lens element including the one or more mirror facets may be disposed between the contact lens surface and the distal portion of the lens element. One or more TIR-inducing air gaps may be defined by the protective cover between an interior surface of the protective cover and the one or more mirror facets of the lens element.

Although the concepts of the present disclosure are described herein with primary reference to ophthamalic lens assemblies such as those used in gonioscopy, it is contemplated that the concepts will enjoy applicability to any type of lens assembly such as, for example and not as a limitation, those utilized in optometry of humans or other species.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
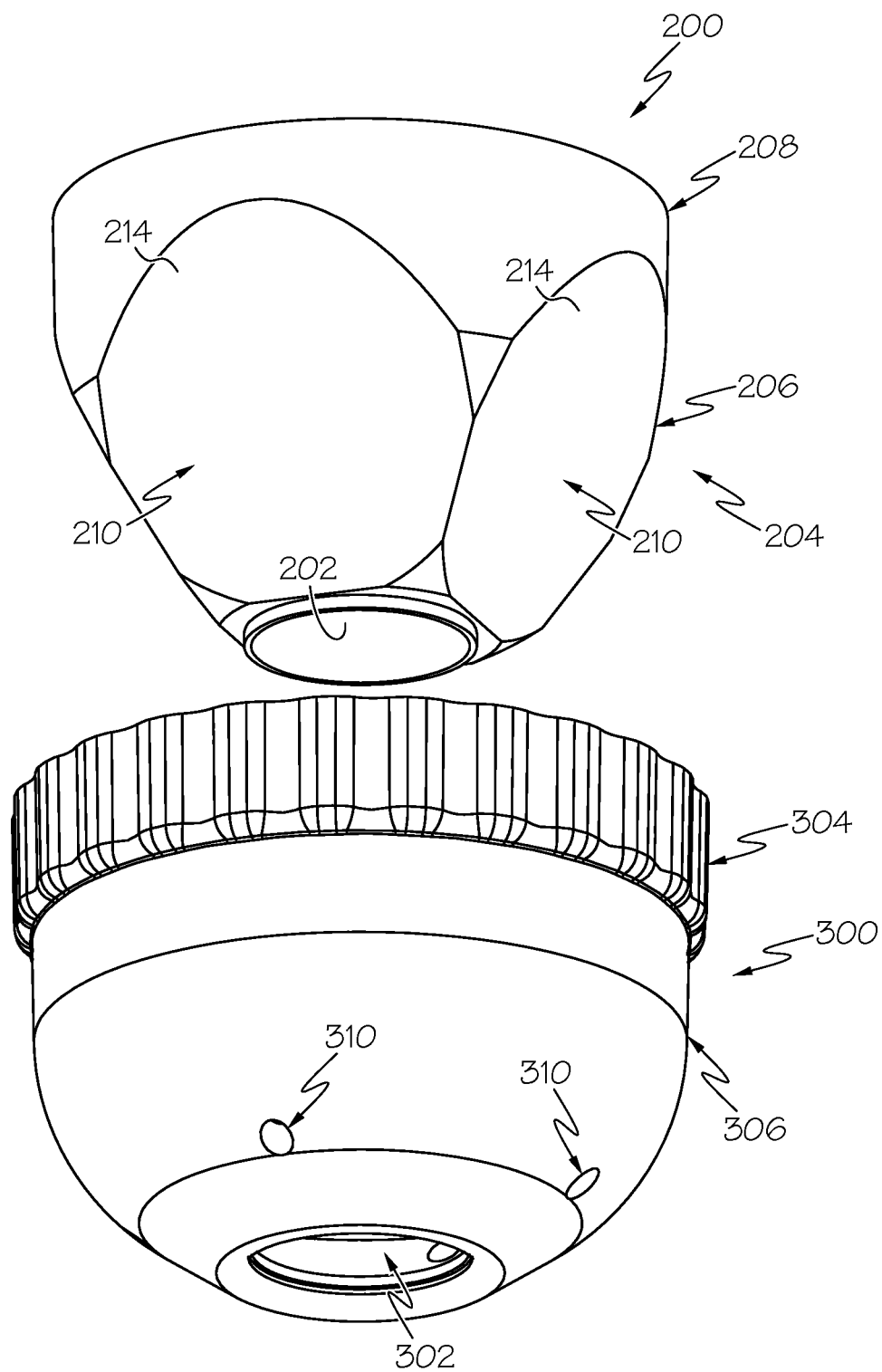
FIG. 1 schematically depicts an exploded perspective view of a lens element and a protective cover, according to one or more embodiments shown and described herein.
Figure 2:
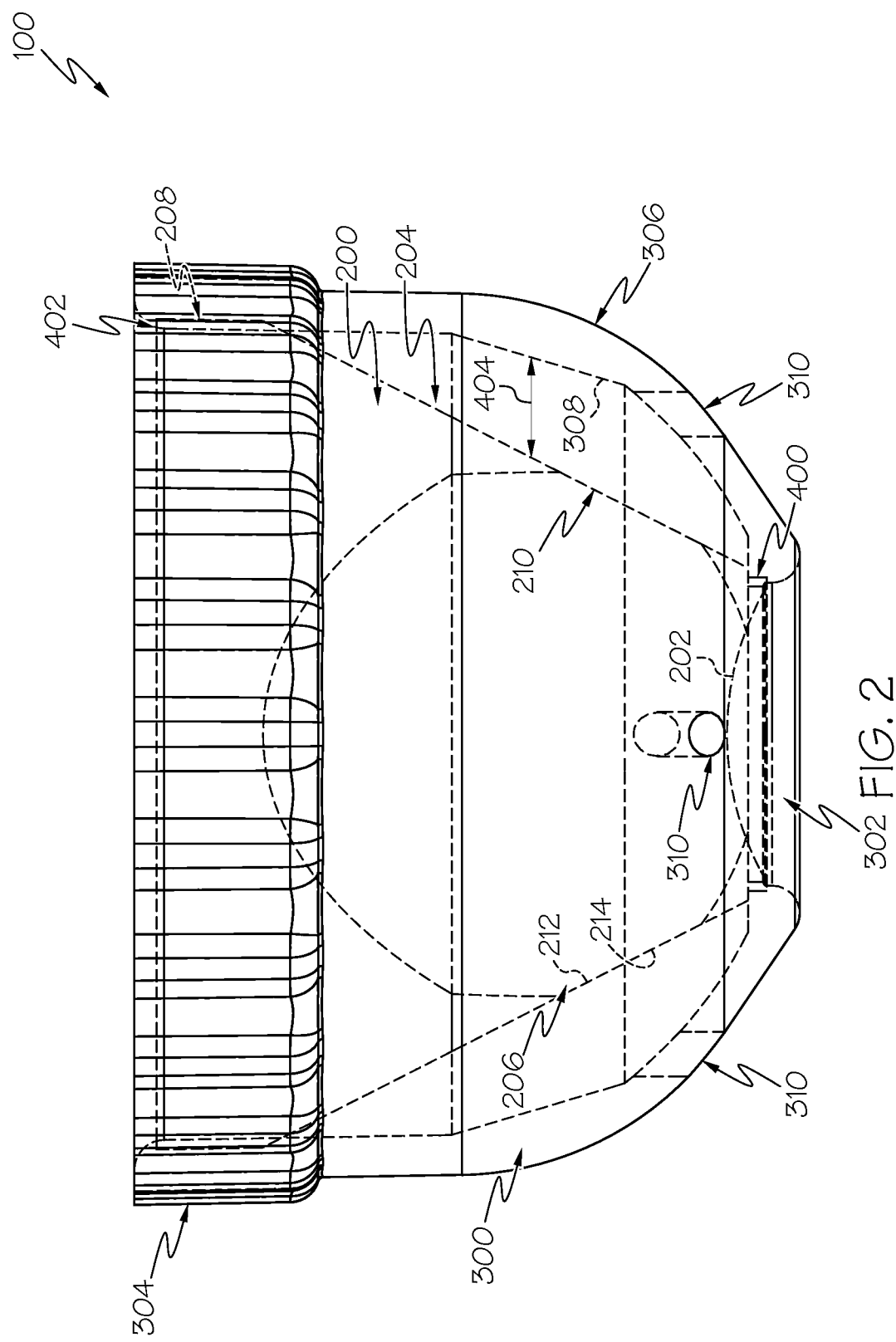
FIG. 2 schematically depicts a perspective view of a lens assembly in which the lens element and the protective cover shown in FIG. 1 are assembled, according to one or more embodiments shown and described herein.

Referring initially to FIGS. 1-2, a lens assembly 100 (FIG. 2) comprises a lens element 200 and a protective cover 300. The lens element 200 comprises a contact lens surface 202 and a faceted optical body 204. The contact lens surface 202 is shaped to contact a portion of a curvature surface of a cornea of an eye. For example, the contact lens surface 202 comprises a concave first optical surface that is placeable in direct contact with the cornea of a patient during use.

The faceted optical body 204 comprises a faceted portion 206 and a distal portion 208. The distal portion 208 of the lens element 200 may be cylindrical though it should be understood that other suitable shapes are within the scope of this disclosure. The faceted portion 206 of the faceted optical body 204 is disposed between the contact lens surface 202 and the distal portion 208 of the faceted optical body 204. The faceted portion 206 comprises one or more mirror facets 210, each mirror facet 210 comprising a respective internal, optically reflective facet 212 (FIG. 2) and an external facet 214 disposed opposite a respective internal, optically reflective facet 212. Each internal, optically reflective facet 212 and respective, opposing external facet 214 of each mirror facet 210 are on co-aligned planes. These mirror facets 210 (and other embodiments of mirror facets described herein and further below) comprise flat angled mirror surfaces to redirect light from specific areas of a patient's eye into a direction the reflected light may be imaged by a viewing device operated by an eye care provider such as an optometrist, for example. The viewing device may be, for example, a slit lamp stereomicroscope.

Referring to FIGS. 1-2, the internal, optically reflective facets 212 comprise respective total-internal-reflective (TIR) surfaces. The internal, optically reflective facets 212 and the contact lens surface 202 form a pathway for TIR activity (which activity is also referenced herein simply as "TIR"). In particular, the mirror facets 210 and one or more TIR-inducing air gaps 404 cooperate to induce TIR activity, as described in greater detail below. The TIR-inducing air gaps permit the use of mirror facets 210 that are "uncoated," i.e., not coated with a reflective coating layer. As such, it is not necessary to utilize reflective metallic coatings to induce optical reflection. These coatings generally increase the complexity and the cost of manufacturing a lens element. Without these relatively expensive coatings, it is much more feasible to introduce the lens assembly 100 as a single-use lens assembly.

Regarding manufacture of the lens assembly 100, the lens element 200 may be fabricated using injection molding and/or using machining and polishing operations. It is contemplated that the contact lens surface 202 and the faceted optical body 204 can be integrally formed. For example, the contact lens surface 202 and the faceted optical body 204 may be integrally formed using injection molding. In alternative embodiments, the contact lens surface 202 and the faceted optical body 204 may be formed as separate pieces that may be adhered or otherwise attached to each other after formation. The attachment may be tailored such that the separate pieces are detachable from each other. For example, it is contemplated that the separate pieces may be formed through injection molding and then attached to one another in a detachable manner.

The lens element 200 may be formed using a polymer material that is optically transparent in the visible range of the electromagnetic spectrum. The lens element 200 may be made of at least an optical material having an index of refraction in a range of from about 1.45 to 1.60. As a non-limited example, the lens element 200 is made of a medical grade acrylic.

The faceted optical body 204 comprises four equidistant mirror facets 210 disposed about a periphery of the faceted portion 206 of the faceted optical body 204. As an example and not a limitation, the lens element 200 may be an ophthalmic lens such as a 4-mirror "Sussmann" style or type lens. In embodiments, the TIR surfaces of the four internal, optically reflective facets 210 reflect illumination into an anterior chamber of an eye and redirects light reflected by the anterior chamber into a direction external to the eye and viewable by an external source.

The protective cover 300 comprises a contact aperture 302 shaped to receive the contact lens surface 202. The protective cover 300 also comprises a grip portion 304, and a facet housing portion 306 comprising an interior surface 308 (FIG. 2) and disposed between the contact aperture 302 and the grip portion 304.

The contact aperture 302 of the protective cover 300 is stretch-fit about a periphery of the contact lens surface 202 to maintain a proximal-side fluid seal 400. The grip portion 304 of the protective cover 300 is stretch-fit about the distal portion 208 of the lens element 200 to maintain a distal-side fluid seal 402.

One or more TIR-inducing air gaps 404 are defined by the facet housing portion 306 of the protective cover 300 between the interior surface 308 of the facet housing portion 306 of the protective cover 300 and the external facets 214 of the faceted portion 206 of the faceted optical body 204. Indeed, when the protective cover 300 is disposed about the lens element 200, air will occupy the TIR-inducing air gaps 404. The air will permit TIR activity to occur when a predetermined, consistent lens substrate-to-air index-of-refraction differential is maintained within the TIR-inducing air gaps 404, as described in greater detail further below.

The protective cover 300 can be made of an elastic and resilient material that is sufficiently rigid to maintain the TIR-inducing air gaps 404 between the interior surface 308 of the protective cover 300 and the external facets 214 under normal use. For example, it is contemplated that the protective cover 300 should be resilient enough to maintain the aforementioned air gaps upon receipt of a compressive gripping force. A "compressive gripping force," as described herein, can be quantified as falling within the range of forces typically associated with handling ophthalmic lens assemblies of the types contemplated herein. For example, the compressive gripping force will often correspond to the force applied when a human user grips the lens assembly for positioning and use in the vicinity of a patient's eye. It is also contemplated that a "compressive gripping force," as described herein, can be quantified as falling within the range of forces typically associated with machinery when used to assist an optometrist with positioning the lens assembly in the vicinity of a patient's eye. The protective cover 300 defines a suitable degree of rigidity and/or compressibility such that the grip portion 304 of the protective cover 300 fully contacts the distal portion 208 of the lens element 200 while maintaining the distal-side fluid seal 402. In some embodiments, the protective cover 300 is molded using a medical grade silicone elastomer.

The TIR-inducing air gaps 404 are sized to maintain a consistent index-of-refraction difference between air and the lens element 200 upon receipt of a compressive gripping force such that TIR activity occurs upon illumination of the TIR surfaces. The interior surface 308 of the protective cover 300 is sufficiently rigid to maintain the TIR-inducing air gaps 404 upon receipt of a compressive gripping force at a size to maintain a consistent index-of-refraction difference between air and the lens element 200 such that TIR activity occurs upon illumination of the TIR surfaces. In embodiments, the consistent index-of-refraction difference is in a range of from about 0.45 to about 0.6.

Further, one or more aeration holes 310 may be disposed in the facet housing portion 306 of the protective cover 300 and in communication with the one or more TIR-inducing air gaps 404. Such aeration holes 310 permit a sterilant to diffuse and migrate into a lens cavity defined by a respective TIR-inducing air gap 404 such that the sterilant may free surfaces defining the lens cavity from the presence of organisms such as potentially harmful living organisms. When the protective cover 300 is disposed about the lens element 200 to form the lens assembly 100, the aeration holes 310 are sized to be sufficient large enough to support the diffusion of the sterilant into and out of the one or more TIR-inducing air gaps 404. And the aeration holes 310 are sized sufficiently small enough, and positioned high enough along a wall defining the facet housing portion 306 of the protective cover 300, to permit the protective cover 300 to prevent fluids, oils, chips, and/or scratches from impacting the mirror facets 210 of the lens element 200.

Figure 3:
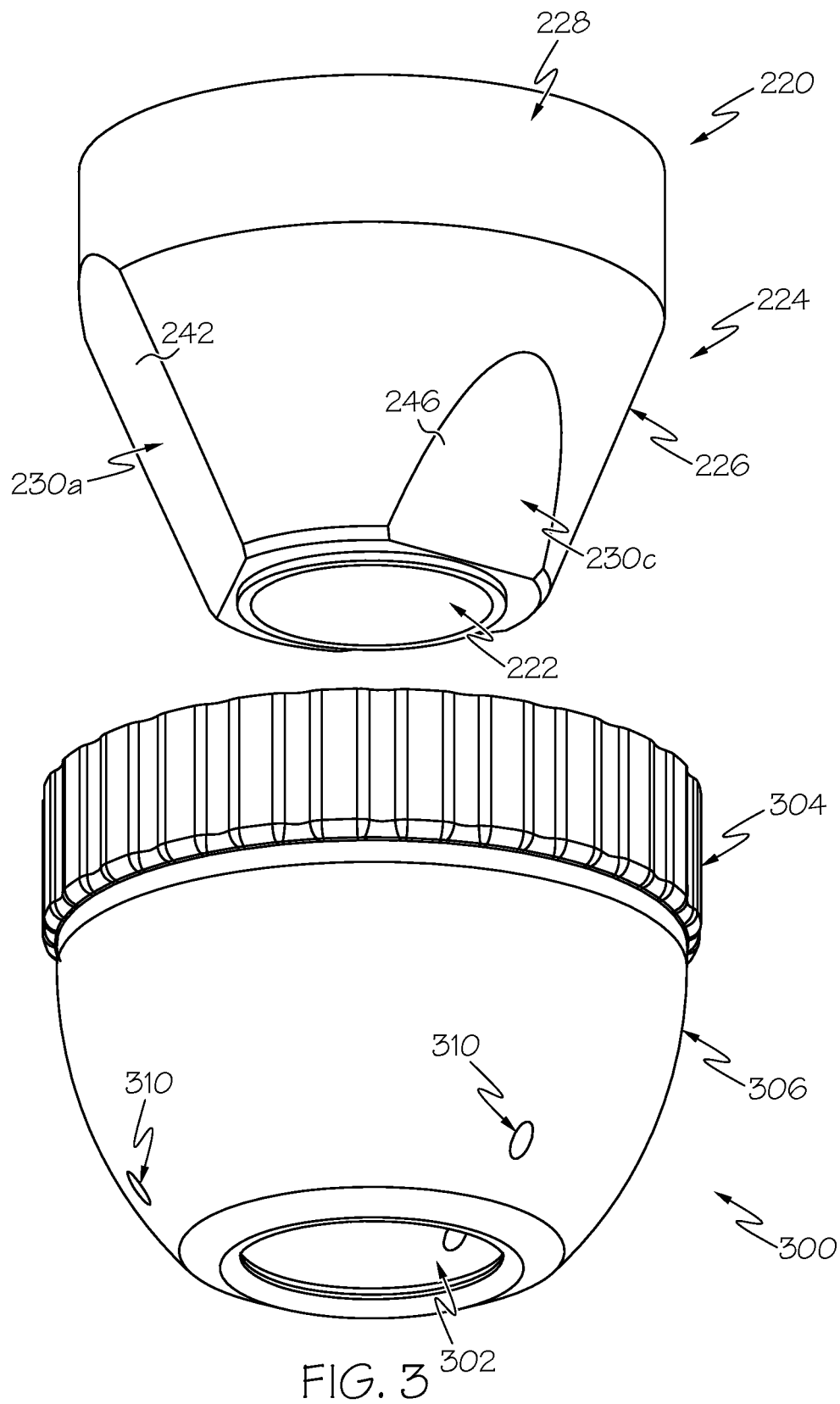
FIG. 3 schematically depicts an exploded perspective view of another lens element and the protective cover of FIG. 1, according to one or more embodiments shown and described herein.
Figure 4:
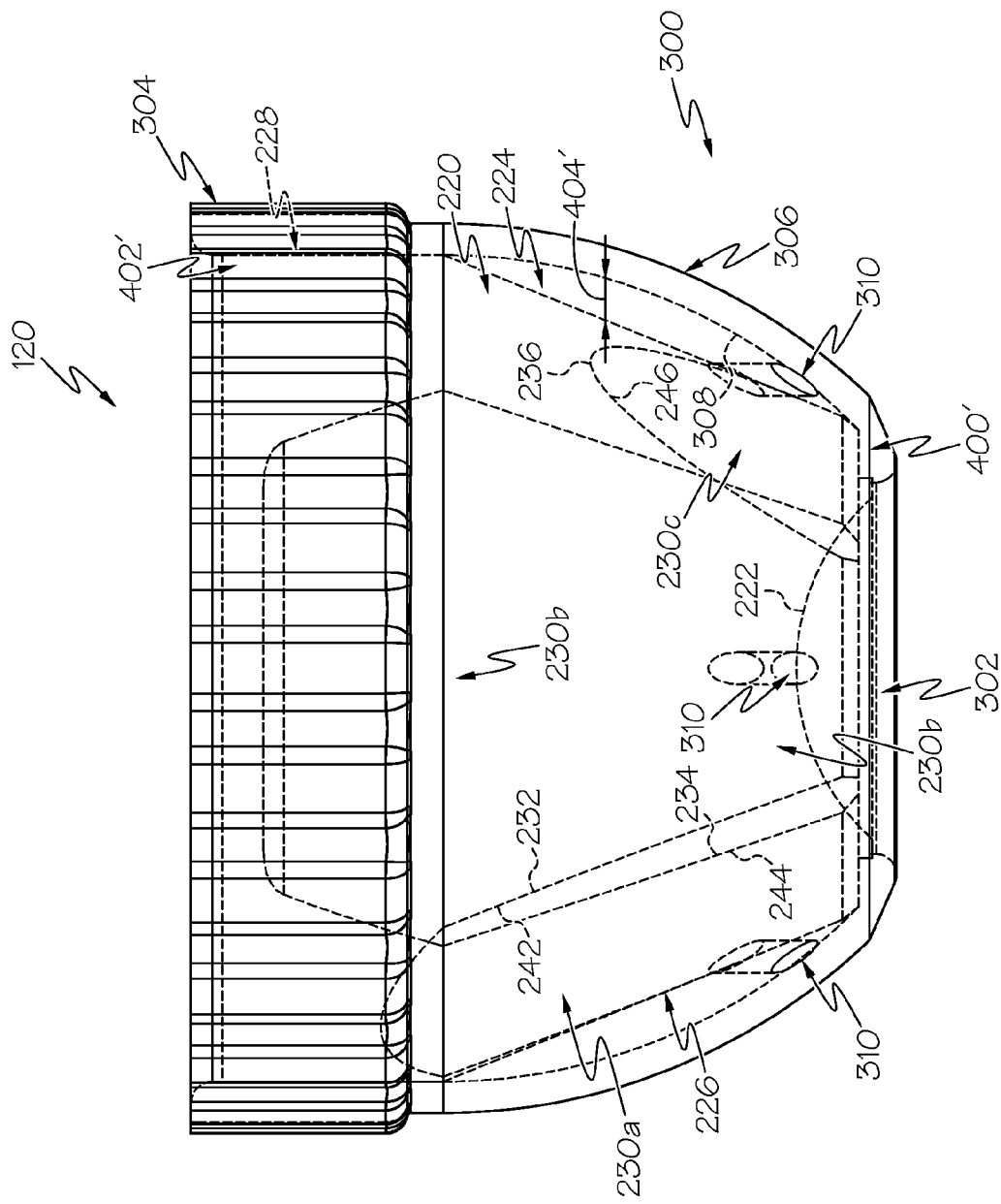
FIG. 4 schematically depicts a perspective view of another lens assembly in which the lens element and the protective cover shown in FIG. 3 are assembled, according to one or more embodiments shown and described herein.

Referring now to FIGS. 3-4, a lens assembly 120 (FIG. 4) is illustrated that is similar to the lens assembly 100. The lens assembly 120 differs from the lens assembly 100 described herein in that the lens element 220 of lens assembly 120 includes a 3-mirror facet structure rather than the 4-mirror facet structure of the lens element 200 of the lens assembly 100. Thus, similar to the lens assembly 100, the lens assembly 120 comprises a lens element 220 and the protective cover 300, and the lens element 220 comprises a contact lens surface 222 and a faceted optical body 224. It is to be understood that a lens element including a single mirror facet or multiple mirror facets (such as a dual mirror facet structure or a 5-or-greater mirror facet structure) is within the scope of this disclosure.

Further similarly, the faceted optical body 224 comprises a faceted portion 226 and a distal portion 228. The faceted portion 226, however, comprises one or more mirror facets 230a, 230b, 230c. Each mirror facets 230a, 230b, 230c respectively comprising internal, optically reflective facets 232, 234, 236 and external facets 242, 244, 246 disposed opposite respective internal, optically reflective facets 232, 234, 236. Each internal, optically reflective facet 232, 234, 236 and respective, opposing external facet 242, 244, 246 of each mirror facet 230a, 230b, 230c are on co-aligned planes. As an example and not a limitation, the lens element 220 may be an ophthalmic lens such as a 3-mirror "Goldmann" style or type lens.

Referring to FIGS. 3-4, the internal, optically reflective facets 232, 234, 236 comprise respective TIR surfaces. The internal, optically reflective facets 232, 234, 236 of respective mirror facets 230a, 230b, 230c and the contact lens surface 222 form a pathway for TIR activity. In particular, the mirror facets 230a, 230b, 230c and the one or more TIR-inducing air gaps 404' cooperate to induce TIR activity. In some embodiments, the mirror facets 230a, 230b, 230c are uncoated. As a non-limiting example, the faceted optical body 224 comprises three mirror facets 230a, 230b, 230c comprising a mid-retina mirror facet 230a dedicated to viewing the mid-retina of the eye, a peripheral retina mirror facet 230b dedicated to viewing the peripheral retina of the eye, and an anterior chamber mirror facet 230c, dedicated to viewing the anterior chamber of the eye. The internal, optically reflective facet 232 and respective external facet 242 are part of an uncoated mid-retina mirror facet 230a. The internal, optically reflective facet 234 and respective external facet 244 are part of an uncoated peripheral retina mirror facet 230b. The internal, optically reflective facet 236 and respective external facet 246 are part of an uncoated anterior chamber mirror facet 230c.

The contact aperture 302 of the protective cover 300 is stretch-fit about a periphery of the contact lens surface 222 to maintain a proximal-side fluid seal 400'. The grip portion 304 of the protective cover 300 is stretch-fit about the distal portion 228 of the lens element 220 to maintain a distal-side fluid seal 402'. One or more TIR-inducing air gaps 404' are defined by the facet housing portion 306 of the protective cover 300 between the interior surface 308 of the facet housing portion 306 of the protective cover 300 and the external facets 242, 244, 246 of the faceted portion 226 of the faceted optical body 224 of the lens element 220. In embodiments, the one or more aeration holes 310 disposed in the facet housing portion 306 of the protective cover 300 are in communication with the one or more TIR-inducing air gaps 404'.

As an example and not a limitation, a method of assembling and using an ophthalmic lens assembly 100, 120, such as for diagnosing and treating conditions of an eye, comprises disposing a protective cover about a lens element including one or more mirror facets that include respective TIR surfaces. A contact lens surface of the lens element is received through a contact aperture of the protective cover. The protective cover is stretch-fit about a periphery of the contact lens surface to maintain a proximal-side fluid seal. The protective cover is stretch-fit about a distal portion of the lens element to maintain a distal-side fluid seal.

For example, with reference to FIGS. 1-4, the protective cover 300 is disposed about one of the lens element 200 or 220, that include the one or more mirror facets 210 or the one or more mirror facets 230a-230c, respectively, which facets 210, 230a-c include respective TIR surfaces. The contact lens surface 202, 222 of the lens element 200, 220 is received through the contact aperture 302 of the protective cover 300. The protective cover 300 is stretch-fit about a periphery of the contact lens surface 202, 222 to maintain a proximal-side fluid seal 400, 400'. The protective cover 300 is stretch-fit about the distal portion 208, 228 of the lens element to maintain a distal-side fluid seal 402, 402'. A faceted portion 206, 226 of the lens element 200 including the one or more mirror facets 210, 230a-230c is disposed between the contact lens surface 202, 222 and the distal portion 208, 228 of the lens element 200, 220. One or more TIR-inducing air gaps 404, 404' are defined by the protective cover 300 between the interior surface 308 of the protective cover 300 and the one or more mirror facets 210, 230a-230c of the lens element 200, 220, respectively. The contact lens surface 202, 222 of the lens element is placed in contact with a portion of a curvature surface of a cornea of the eye, and illumination is reflected into the eye via the TIR surfaces and light reflected by the eye is redirected via the TIR surfaces into a direction for external viewing.

The method further may comprise applying a sterilant through one or more aeration holes disposed in a facet housing portion comprising the interior surface of the protective cover such that the sterilant diffuses into a respective TIR-inducing air gap aligned with the a respective aeration hole. For example, the sterilant may be applied through the one or more aeration holes 310 disposed in a facet housing portion 306 comprising the interior surface 308 of the protective cover 300 such that the sterilant diffuses into a respective TIR-inducing air gap 404, 404' aligned with a respective aeration hole 310. The sterilant may be, for example, ethylene oxide gas.

TIR activity by a lens element, such as the lens element 200 or 220, along with a protective cover such as the protective cover 300 to create a lens assembly is complicated and/or restricted in practice if a mirror facet surface of the lens element becomes wet by fluids and particulates such as through tears, saline solution, optical coupling solution, and the like. For example, the presence of the fluid elements adjust the difference in the index-of-refraction within the lens assembly to a level that may not be suitable for TIR activity. Thus, the fluid seals created between the protective cover 300 and the lens element 200, 220 prevent a wetting of mirror facets of the lens element 200, 220 such that TIR activity may occur as a suitable difference in the index-of-refraction within the lens assembly may be maintained. Such fluid seals between the protective cover 300 and the lens element 200 or 220 further prevent contamination and/or damage of the lens elements. Further, as the mirror facets of the lens element 200, 220 may not be coated with, for example, a reflective metallic coating but rather rely in the TIR-inducing air gaps as described in the lens assembly embodiments herein that create sealed-in zones near the reflective mirror facet surfaces of the lens elements 200, 220 to induce TIR activity, the lens elements and thus lens assemblies in total tend to be less expensive to manufacture than when reflective metallic coatings are applied and are suitable for single-use, disposable applications. By such single-usage, there is less of a chance of cross-contamination between patients or persons on which shared, multiple-use lens assemblies might otherwise be used.

It is also noted that recitations herein of "at least one" component, element, etc., should not be used to create an inference that the alternative use of the articles "a" or "an" should be limited to a single component, element, etc.

For the purposes of describing and defining the present invention it is noted that the terms "substantially" and "approximately" and "about" are utilized herein to represent the inherent degree of uncertainty that may be attributed to any quantitative comparison, value, measurement, or other representation. The terms "substantially" and "approximately" and "about" are also utilized herein to represent the degree by which a quantitative representation may vary from a stated reference without resulting in a change in the basic function of the subject matter at issue. For example, utilization of such terms may represent a degree by which a quantitative representation varies within reasonable tolerances from a stated reference.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A lens assembly comprising a lens element and a protective cover, wherein:
    the lens element comprises a contact lens surface and a faceted optical body comprising a faceted portion and a distal portion;
    the faceted portion is disposed between the contact lens surface and the distal portion;
    the faceted portion comprises one or more mirror facets comprising respective one or more internal, optically reflective facets and one or more external facets disposed opposite respective internal, optically reflective facets;
    the one or more internal, optically reflective facets comprise respective one or more total-internal-reflective (TIR) surfaces;
    the one or more internal, optically reflective facets and the contact lens surface form a pathway for TIR activity;
    the protective cover comprises a contact aperture shaped to receive the contact lens surface, a grip portion, and a facet housing portion comprising an interior surface and disposed between the contact aperture and the grip portion;
    the contact aperture of the protective cover is stretch-fit about a periphery of the contact lens surface to maintain a proximal-side fluid seal;
    the grip portion of the protective cover is stretch-fit about the distal portion of the lens element to maintain a distal-side fluid seal; and
    one or more TIR-inducing air gaps are defined by the facet housing portion of the protective cover between the interior surface of the facet housing portion of the protective cover and the one or more external facets of the faceted portion of the faceted optical body.

2. The lens assembly of claim 1, wherein the contact lens surface is shaped to contact a portion of a curvature surface of a cornea of an eye.

3. The lens assembly of claim 1, further comprising one or more aeration holes disposed in the facet housing portion of the protective cover and in communication with the one or more TIR-inducing air gaps.

4. The lens assembly of claim 1, wherein the TIR-inducing air gaps are sized to maintain a consistent index-of-refraction difference between air and the lens element upon receipt of a compressive gripping force such that TIR activity occurs upon illumination of the TIR surfaces.

5. The lens assembly of claim 1, wherein the interior surface of the protective cover is sufficiently rigid to maintain the TIR-inducing air gaps upon receipt of a compressive gripping force at a size to maintain a consistent index-of-refraction difference between air and the lens element such that TIR activity occurs upon illumination of the TIR surfaces.

6. The lens assembly of claim 5, wherein the consistent index-of-refraction difference is in a range of from about 0.45 to about 0.6.

7. The lens assembly of claim 1, wherein the lens element is formed using a polymer material that is optically transparent in a visible range of an electromagnetic spectrum.

8. The lens assembly of claim 1, wherein the lens element is made of at least an optical material having an index of refraction in a range of from about 1.45 to 1.60.

9. The lens assembly of claim 1, wherein the lens element is made of a medical grade acrylic.

10. The lens assembly of claim 1, wherein the contact lens surface and the faceted optical body are detachable from one another.

11. The lens assembly of claim 1, wherein the contact lens surface and the faceted optical body are integrally formed via injection molding.

12. The lens assembly of claim 1, wherein the lens assembly is a single-use assembly.

13. The lens assembly of claim 1, wherein the protective cover is made of an elastic and resilient material that is sufficiently rigid to maintain the TIR-inducing air gaps between the interior surface of the protective cover and the one or more external facets upon receipt of a compressive gripping force.

14. The lens assembly of claim 1, wherein the protective cover defines a suitable degree of at least one of rigidity and compressibility such that the grip portion of the protective cover fully contacts the distal portion of the lens element while maintaining the distal-side fluid seal.

15. The lens assembly of claim 14, wherein the distal portion of the lens element is cylindrical.

16. The lens assembly of claim 1, wherein the protective cover is molded using a medical grade silicone elastomer.

17. The lens assembly of claim 1, wherein the one or more mirror facets are uncoated.

18. The lens assembly of claim 1, wherein the faceted optical body comprises four equidistant mirror facets disposed about a periphery of the faceted portion of the faceted optical body.

19. The lens assembly of claim 18, wherein the TIR surfaces of the internal, optically reflective facets of the four equidistant mirror facets reflect illumination into an anterior chamber of an eye and redirects light reflected by the anterior chamber into a direction external to the eye and viewable by an external source.

20. The lens assembly of claim 1, wherein the faceted optical body comprises three mirror facets comprising a mid-retina mirror facet dedicated to viewing a mid-retina of an eye, an anterior chamber mirror facet dedicated to viewing an anterior chamber of the eye, and a peripheral retina mirror facet dedicated to viewing a peripheral retina of the eye.

21. A method of assembling and using an ophthalmic lens assembly, the method comprising:
 disposing a protective cover about a lens element including one or more mirror facets that include respective TIR surfaces, wherein:
  a contact lens surface of the lens element is received through a contact aperture of the protective cover,
  the protective cover is stretch-fit about a periphery of the contact lens surface to maintain a proximal-side fluid seal;
  the protective cover is stretch-fit about a distal portion of the lens element to maintain a distal-side fluid seal;
  a faceted portion of the lens element including the one or more mirror facets is disposed between the contact lens surface and the distal portion of the lens element; and
  one or more TIR-inducing air gaps are defined by the protective cover between an interior surface of the protective cover and the one or more mirror facets of the lens element;
 placing the contact lens surface of the lens element in contact with a portion of a curvature surface of a cornea of an eye; and
 reflecting illumination into the eye via the TIR surfaces and redirecting light reflected by the eye via the TIR surfaces into a direction for external viewing.

22. The method of claim 21, further comprising applying a sterilant through one or more aeration holes disposed in a facet housing portion comprising the interior surface of the protective cover such that the sterilant diffuses into a respective TIR-inducing air gap aligned with a respective aeration hole.

23. The method of claim 22, wherein the sterilant is ethylene oxide gas.

24. A method of assembling an ophthalmic lens assembly by disposing a protective cover about a lens element including one or more mirror facets that include respective TIR surfaces, wherein:
 a contact lens surface of the lens element is received through a contact aperture of the protective cover,
 the protective cover is stretch-fit about a periphery of the contact lens surface to maintain a proximal-side fluid seal;
 the protective cover is stretch-fit about a distal portion of the lens element to maintain a distal-side fluid seal;
 a faceted portion of the lens element including the one or more mirror facets is disposed between the contact lens surface and the distal portion of the lens element; and
 one or more TIR-inducing air gaps are defined by the protective cover between an interior surface of the protective cover and the one or more mirror facets of the lens element.

* * * * *